US 12,383,440 B2

(12) United States Patent
Cobbaert et al.

(10) Patent No.: US 12,383,440 B2
(45) Date of Patent: Aug. 12, 2025

(54) ELASTICISED ABSORBENT ARTICLE

(71) Applicants: ONTEX BV, Buggenhout (BE);
ONTEX GROUP NV, Erembodegem (BE)

(72) Inventors: Dries Cobbaert, Liedekerke (BE);
Nathalie Van Sande, Maarkedal (BE)

(73) Assignees: ONTEX BV, Buggenhout (BE); ONEX GROUP NV, Erembodegem (BE)

(*) Notice: Subject to any disclaimer, the term of this patent is extended or adjusted under 35 U.S.C. 154(b) by 1021 days.

(21) Appl. No.: 17/272,761

(22) PCT Filed: Sep. 4, 2019

(86) PCT No.: PCT/EP2019/073584
§ 371 (c)(1),
(2) Date: Mar. 2, 2021

(87) PCT Pub. No.: WO2020/049047
PCT Pub. Date: Mar. 12, 2020

(65) Prior Publication Data
US 2021/0186775 A1    Jun. 24, 2021

(30) Foreign Application Priority Data

Sep. 4, 2018    (EP) .................................... 18192449

(51) Int. Cl.
*A61F 13/49*     (2006.01)
*A61F 13/496*    (2006.01)

(52) U.S. Cl.
CPC .. *A61F 13/49012* (2013.01); *A61F 13/49001* (2013.01); *A61F 13/496* (2013.01)

(58) Field of Classification Search
CPC .............. A61F 13/496; A61F 13/49012; A61F 13/49001; A61F 13/49009;
(Continued)

(56) References Cited

U.S. PATENT DOCUMENTS 6,476,289 B1    11/2002    Buell et al.
6,552,245 B1     4/2003    Roessler et al.
(Continued)

FOREIGN PATENT DOCUMENTS

EP    3369407 A1    9/2018
JP    H1043235 A    2/1998
(Continued)

OTHER PUBLICATIONS

International Search Report and Written Opinion for PCT/EP2019/073584, mailed Oct. 24, 2019.
(Continued)

*Primary Examiner* — Susan S Su
(74) *Attorney, Agent, or Firm* — VIVICAR Law, PLLC (57) ABSTRACT

The present invention relates to an absorbent article (1), preferably an incontinence pant-like diaper, comprising a chassis (2), a front waist region (3), a back waist region (4) and a crotch region (5) extending between said front and back waist regions (3,4); wherein the front and back waist regions (3,4) are joinable to each other and wherein, when joined, a waist-opening is formed and a pair of leg-openings are formed by one or more crotch-leg-peripheral-edges (17,17') and front and back waist-leg-peripheral-edges (18, 18',19,19'), and wherein first and second front waist-leg-peripheral-edges (18,18') extend from a first position (20, 20') proximal to the crotch region (5) to a second position (21,21') distal therefrom and proximal to a lateral edge (15,15') of the front waist region (3), said first and second front waist-leg-peripheral-edges (18,18') being oppositely disposed from the longitudinal axis. It is characterized in that distance D extending parallel to the longitudinal axis (Y-Y) between the front waist end (13) and a fifth position (22,22') along the first and second front waist-leg-peripheral-edges (18,18') which is closest to the front waist end
(Continued)

(13), is smaller than length L of a front waist lateral edge (15,15') extending parallel to the longitudinal axis (Y-Y).

18 Claims, 4 Drawing Sheets

(58) Field of Classification Search
CPC ........ A61F 13/49011; A61F 13/49058–49061; A61F 13/49007–4902; A61F 2013/49022–49057
See application file for complete search history.

(56) References Cited

U.S. PATENT DOCUMENTS

| | | | |
|---|---|---|---|
| 7,785,307 | B2 | 8/2010 | Wennerback |
| 2004/0243086 | A1 | 12/2004 | VanGompel et al. |
| 2008/0125741 | A1 | 5/2008 | Tsuji et al. |
| 2008/0287899 | A1 | 11/2008 | Morrell-Schwartz et al. |
| 2011/0098668 | A1 | 4/2011 | Thorson et al. |
| 2013/0165886 | A1 | 6/2013 | Glaug et al. |
| 2018/0125728 | A1* | 5/2018 | Matsumiya ........ A61F 13/49061 |
| 2020/0030157 | A1* | 1/2020 | Lee ................... A61F 13/49061 |
| 2020/0375814 | A1* | 12/2020 | Tsunoda ................. B32B 33/00 |

FOREIGN PATENT DOCUMENTS

| | | |
|---|---|---|
| WO | 2003047488 A1 | 6/2003 |
| WO | 2004078082 A1 | 9/2004 |
| WO | 2004078084 A1 | 9/2004 |
| WO | 2006093439 A1 | 9/2006 |
| WO | 2009157835 A1 | 12/2009 |
| WO | 2016101196 A1 | 6/2016 |
| WO | 2016114946 A1 | 7/2016 |
| WO | 2016114947 A1 | 7/2016 |
| WO | 2017169381 A1 | 10/2017 |
| WO | 2018111298 A1 | 6/2018 |
| WO | 2018153106 A1 | 8/2018 |
| WO | 2020049047 A1 | 3/2020 |

OTHER PUBLICATIONS

Enclosure O11 to Opposition by Schoepf Patrick to European Patent No. 3620144, dated Apr. 28, 2022 ("grounds of opposition Hartmann AG" and English translation).
Enclosures O8-O10 to Opposition by Schoepf Patrick to European Patent No. 3620144, dated Apr. 28, 2022 ("public prior use").
English Translations of Anlages 1.5, 1.11, 1.13, and 2.4 from Enclosures O8-O10 to Opposition by Schoepf Patrick to European Patent No. 3620144, dated Apr. 28, 2022 ("public prior use").
Opposition by Essity Hygiene and health Ahtiebolag to European Patent No. 3620144, dated Apr. 28, 2022.
Opposition by Schoepf Patrick to European Patent No. 3620144, dated Apr. 28, 2022.
Opposition to European Patent No. 3620143, dated Feb. 9, 2023.

* cited by examiner

ELASTICISED ABSORBENT ARTICLE

CROSS-REFERENCE TO RELATED APPLICATIONS

This application is the national stage application of corresponding international application number PCT/EP2019/073584, filed Sep. 4, 2019, which claims priority to and the benefit of European application no. 18192449.9, filed Sep. 4, 2018, which is hereby incorporated by reference in its entirety.

TECHNICAL FIELD

The invention pertains to the technical field of absorbent hygiene products. In particular, the present invention relates to an absorbent article for absorbing body fluids and exudates, such as urine and fecal material. More particularly, the present invention relates to absorbent garments, such as disposable incontinence pants, which are configured to collect and contain fecal material and avoid leakage.

BACKGROUND

Absorbent articles having defined core and chassis regions are supposed to have a comfortable fit about the wearer. Especially for hygiene absorbent articles like pant articles like pant diapers, sanitary pants and incontinence pants it is also desirable that the articles are capable of being pulled up and down over the hips of the wearer to allow the wearer or caregiver to easily put on and remove the article when it has been soiled. It is known to make such absorbent pants with elasticized stretchable side portions and waist portion, usually comprising elastic members, such as elastic threads, contractibly affixed between the backsheet and the topsheet.

It is further known to make portions of the chassis of absorbent articles of an elastic material, such as stretch-bonded laminates. Such laminates may include a layer of meltblown elastomeric fibers which have been stretched and sandwiched between outer layers of spunbonded webs.

U.S. Pat. No. 6,552,245 discloses an extensible outer cover for an absorbent article which provides a certain permanent deformation when subjected to a tensile force. The extensible outer cover comprises a necked laminate in the form of one layer of a necked non-elastic film and one layer of an elastic film. The films may be breathable.

WO 03/047488 discloses an elastic laminate comprising an elastic film which on opposite sides is bonded to first and second non-elastic fibrous layers. The laminate is made by bonding the non-elastic fibrous layers to the elastic film layer and subsequently stretching the composite material, causing the non-elastic materials to break. The elastic film material may be of a breathable material. The laminate may be incorporated in an absorbent article.

US 2004/0243086 discloses a disposable pant-like undergarment having stretchable front and back portions, for example made of an elastic laminate. An absorbent assembly is secured to the front and back portions.

Further examples of absorbent articles which in part are made of elastic laminates are found in U.S. Pat. No. 6,476,289 and JP 10043235.

U.S. Pat. No. 7,785,307 recognized that to obtain good fit, improved comfort and security against leakage, it is important that absorbent articles have dimensions which match the relative dimensions of the wearer. The relative dimensions of the article are also important, so that the components or regions of the article are not excessively large or small relative to each other. The overall dimensions of the article and relative dimensions of its components may also be adjusted so as to obtain an article with a more pant-like appearance. The disclosed articles thus comprise elasticized waist portions and a geometry of the front and back regions of the article arranged such that the surface area of the front half of the article is less than (i.e. 80-90% of the surface area) the surface area of the back half of the article.

European patent application EP17159249.6 filed on 3 Mar. 2017 discloses that to limit crease formation and thereby ensure good fit and security against leakage, it is important to ensure that a first elastified surface area between the crotch region and the front portion is sufficiently small compared to a second elastified surface area between the crotch region and the back portion.

Nevertheless, the improvement brought by this latter document is mainly directed to the back of the absorbent article and there is still need for improvement of the properties of absorbent articles comprising an elastic web material, such as an elastic laminate, particularly their fit in the front part of the article, in particular in the region of the article which will be worn close to the groin region of the wearer, to limit crease formation at this specific region, to more closely attain the look and feel of standard underwear and to provide excellent security against leakage.

SUMMARY OF THE INVENTION

The present invention provides an absorbent hygiene product, suitable to be worn around the lower torso of a wearer, such as disposable adult incontinence pants, according to claim 1.

In an aspect, the present invention further comprises one or more side barriers extending along the crotch region, preferably comprising one or more leg cuffs and one or more elastics joined thereto, said barriers arranged to further adhere to a portion of the legs of a subject when wearing the absorbent article. Preferably, the absorbent article comprises at least two said barriers disposed in opposite facing positions proximal to lateral edges of the crotch region and wherein the longitudinal axis extends therebetween. Preferably, the barriers being arranged to provide tension over the length of the crotch region in a direction substantially parallel to the longitudinal axis.

The product of the present invention overcomes the problems of prior art products, as it enables to not only provide improved fit that snuggly adheres to the body, in particular in the region of the article which will be worn close to the groin region of the wearer, but further surprisingly reduces the risk of leakage whilst providing the necessary freedom for movement to the wearer and an underwear-like feel.

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The expression "% by weight" (weight percent), here and throughout the description unless otherwise defined, refers to the relative weight of the respective component based on the overall weight of the formulation.

The recitation of numerical ranges by endpoints includes all numbers and fractions subsumed within that range, as well as the recited endpoints.

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinence briefs, training pants, diaper holders and liners, sanitary napkins and the like, as well as surgical bandages and sponges. Absorbent articles preferably comprise a longitudinal axis and a transversal axis perpendicular to said longitudinal axis. The longitudinal axis is hereby conventionally chosen in the front-to-back direction of the article when referring to the article being worn, and the transversal axis is conventionally chosen in the left-to-right direction of the article when referring to the article being worn. Disposable absorbent articles can include a liquid pervious top sheet, a back sheet joined to the top sheet, and an absorbent core positioned and held between the top sheet and the back sheet. The top sheet is operatively permeable to the liquids that are intended to be held or stored by the absorbent article, and the back sheet may or may not be substantially impervious or otherwise operatively impermeable to the intended liquids. The absorbent article may also include other components, such as liquid wicking layers, liquid intake layers, liquid distribution layers, transfer layers, barrier layers, wrapping layers and the like, as well as combinations thereof. Disposable absorbent articles and the components thereof can operate to provide a body-facing surface and a garment-facing surface.

An incontinence absorbent article, such as a diaper, comprises a front waistband region, a back waistband region, an intermediate crotch region which interconnects the front and rear waistband regions. When used herein, reference to a "front" portion refers to that part of the diaper which is generally located on the front of an incontinent person when in use. Reference to the "rear" portion refers to the portion of the diaper generally located at the rear of the incontinent person when in use, and reference to the "crotch" portion refers to that portion which is generally located between the legs of an incontinent person when in use. The crotch region is an area where repeated fluid surge typically occurs.

Preferably, a diaper comprises a liquid permeable "top sheet", a liquid impermeable "back sheet", and an "absorbent medium" disposed between the top sheet and the back sheet. The top sheet, back sheet and the absorbent medium could be made from any suitable material known to the person skilled in the art. The top sheet is generally located at or near the bodyside surface of the article, while the back sheet is generally located at or near the garment-side surface of the article. Optionally, the article may comprise one or more separate layers which are in addition to the back sheet and are interposed between the back sheet and the absorbent medium. Top sheet and back sheet are connected or otherwise associated together in an operable manner.

The "absorbent medium" or "absorbent core" or "absorbent body" is the absorbent structure disposed between the top sheet and the back sheet of the absorbent article in at least the crotch region of the absorbent article and is capable of absorbing and retaining liquid body exudates. The size and the absorbent capacity of the absorbent medium should be compatible with the size of the intended wearer and the liquid loading imparted by the intended use of the absorbent article. Further, the size and the absorbent capacity of the absorbent medium can be varied to accommodate wearers ranging from infants through adults. It may be manufactured in a wide variety of shapes (for example, rectangular, trapezoidal, T-shape, I-shape, hourglass shape, etc.) and from a wide variety of materials. Examples of commonly occurring absorbent materials are cellulosic fluff pulp, tissue layers, highly absorbent polymers (so called superabsorbent polymer particles (SAP)), absorbent foam materials, absorbent nonwoven materials or the like. It is common to combine cellulosic fluff pulp with superabsorbent polymers in an absorbent material.

"Acquisition and distribution layer", "ADL" or "surge management portion" refers to a sub-layer which preferably is a nonwoven wicking layer under the top sheet of an absorbent product, which speeds up the transport and improves distribution of fluids throughout the absorbent core. The surge management portion is typically less hydrophilic than the retention portion, and has the ability to quickly collect and temporarily hold liquid surges, and to transport the liquid from its initial entrance point to other parts of the absorbent structure, particularly the retention portion. This configuration can help prevent the liquid from pooling and collecting on the portion of the absorbent garment positioned against the wearer's skin, thereby reducing the feeling of wetness by the wearer. Preferably, the surge management portion is positioned between the top sheet and the retention portion.

The term "adhesive" as used herein is intended to refer to any suitable hot melt, water or solvent borne adhesive that can be applied to a surface of a film layer in the required pattern or network of adhesive areas to form the film-nonwoven laminate of the present invention. Accordingly, suitable adhesives include conventional hot melt adhesives, pressure-sensitive adhesives and reactive adhesives (i.e., polyurethane).

As used herein, the term "adhesive bonding" means a bonding process which forms a bond by application of an adhesive. Such application of adhesive may be by various processes such as slot coating, spray coating and other topical applications. Further, such adhesive may be applied within a product component and then exposed to pressure such that contact of a second product component with the adhesive containing product component forms an adhesive bond between the two components.

As used herein, an "airformed web" refers to a material comprising cellulosic fibers such as those from fluff pulp that have been separated, such as by a hammermilling process, and then deposited on a porous surface without a substantial quantity of binder fibers present. Airfelt materials used as the absorbent core in many diapers, for example, are a typical example of an airformed material.

As used herein, an "airlaid web" is a fibrous structure formed primarily by a process involving deposition of air-entrained fibers onto a mat, typically with binder fibers present, and typically followed by densification and thermal bonding. In addition to traditional thermally bonded airlaid structures (those formed with non-tacky binder material present and substantial thermally bonded), the scope of the term "airlaid" according to the present invention can also include coform, which is produced by combining air-entrained dry, dispersed cellulosic fibers with meltblown synthetic polymer fibers while the polymer fibers are still tacky. Further, an airformed web to which binder material is subsequently added can be considered within the scope of the term "airlaid" according to the present invention. Binder can be added to an airformed web in liquid form (e. g., an aqueous solution or a melt) by spray nozzles, direction injection or impregnation, vacuum drawing, foam impregnation, and so forth. Solid binder particles can also be added by mechanical or pneumatic means.

As used therein, the term "associated" encompasses configurations in which top sheet is directly joined to back sheet by affixing top sheet directly to back sheet, and configurations wherein top sheet is joined to back sheet by affixing top sheet to intermediate members which in turn are affixed to back sheet. Top sheet and back sheet can be affixed directly to each other by attachment means such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix top sheet to back sheet. It should be readily appreciated that the above-described attachment means may also be employed to interconnect and assemble together the various other component parts of the article described herein.

The terms "back section" and "rear back section" are used herein as synonyms and refer to the area of the absorbent article which is contact with the back of the wearer when the absorbent article is worn.

The term "back sheet" refers to a material forming the outer cover of the absorbent article. The back sheet prevents the exudates contained in the absorbent structure from wetting articles such as bedsheets and overgarments which contact the disposable absorbent article. The back sheet may be a unitary layer of material or may be a composite layer composed of multiple components assembled side-by-side or laminated. The back sheet may be the same or different in different parts of the absorbent article. At least in the area of the absorbent medium the back sheet comprises a liquid impervious material in the form of a thin plastic film, e.g. a polyethylene or polypropylene film, a nonwoven material coated with a liquid impervious material, a hydrophobic nonwoven material, which resists liquid penetration, or a laminate of a plastic film and a nonwoven material. The back sheet material may be breathable so as to allow vapour to escape from the absorbent material, while still preventing liquids from passing there through. Examples of breathable back sheet materials are porous polymeric films, nonwoven laminates of spunbond and meltblown layers and laminates of porous polymeric films and nonwoven materials.

The terms "belly section" and "front belly section" are used herein as synonyms and refer to the area of the absorbent article which is contact with the belly of the wearer when the absorbent article is worn.

A belt can be attached to the diaper to provide a mechanism for holding the diaper on the wearer. The belt can be either one continuous belt attached to the diaper at the front and/or rear waistband region thereof or could be two separate belt portions, each attached to a respective side of the front and/or rear waistband region of the diaper. When a belt is present, the absorbent article is often referred to as a belt diaper. A "belt diaper" is intended to encompass the lower portion of the wearer's trunk like a pair of absorbent pants. If the belt, for example, consists of two belt portions extending on either side of the rear waistband region of the diaper, the belt diaper can be attached to a wearer in the following manner: the two belt portions are first fastened around the waist of the wearer while the front end of the diaper hangs down between the legs of the wearer. Once the belt portions have been joined together, the wearer can reach between his or her legs to draw up the absorbent garment between the legs and to attach the free end of the diaper to the belt portion. The attachment of the two belt portions and the attachment of the belt to the diaper typically occurs by fastening means such as hook and loop fasteners, e.g. VELCRO®, or adhesive fasteners. However, it should be understood that other types of fastening devices are possible, including but not limited to, adhesive, pressure buttons, buttons and button holes, knots, and strings. The belt diaper can also be made so that the belt is fastened to the front portion of the product and is secured around the back of the wearer. In this case, the absorption product will be hanging down in the front and will be secured to the belt in the back.

The term "blend" means a mixture of two or more polymers while the term "alloy" means a sub-class of blends wherein the components are immiscible but have been compatibilized.

As used herein, the "body-facing" or "bodyside" surface means that surface of the article or component which is intended to be disposed toward or placed adjacent to the body of the wearer during ordinary use, while the "outward", "outward-facing" or "garment-side" surface is on the opposite side, and is intended to be disposed to face away from the wearer's body during ordinary use. Such outward surface may be arranged to face toward or placed adjacent to the wearer's undergarments when the absorbent article is worn.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

The term "breathable" refers to layers, preferably films or elastic laminates, having a water vapor transmission rate (WVTR) of at least 300 grams/m$^2$-24 hours.

"Carded web" refers to webs that are made from staple fibers that are sent through a combing or carding unit, which opens and aligns the staple fibers in the machine direction to form a generally machine direction-oriented fibrous nonwoven web. The web is then bonded by one or more of several known bonding methods. Bonding of nonwoven webs may be achieved by a number of methods; powder bonding, wherein a powdered adhesive or a binder is distributed through the web and then activated, usually by heating the web and adhesive with hot air; pattern bonding, wherein heated calendar rolls or ultrasonic bonding equipment are used to bond the fibers together, usually in a localized bond pattern, though the web can be bonded across its entire surface if so desired; through-air bonding, wherein air which is sufficiently hot to soften at least one component of the web is directed through the web; chemical bonding using, for example, latex adhesives that are deposited onto the web by, for example, spraying; and consolidation by mechanical methods such as needling and hydroentanglement.

As used herein, the term "cellulosic" is meant to include any material having cellulose as a major constituent, and specifically comprising at least 50 percent by weight cellulose or a cellulose derivative. Thus, the term includes cotton, typical wood pulps, nonwoody cellulosic fibers, cellulose acetate, cellulose triacetate, rayon, thermomechanical wood pulp, chemical wood pulp, debonded chemical wood pulp, milkweed, or bacterial cellulose.

"Chassis" refers to a foundational constituent of an absorbent article upon which the remainder of the structure of the article is built up or overlaid, e.g., in a diaper, the structural elements that give the diaper the form of briefs or pants when configured for wearing, such as a back sheet, a top sheet, or a combination of a top sheet and a back sheet.

"Coform" as used herein is intended to describe a blend of meltblown fibers and cellulose fibers that is formed by air forming a meltblown polymer material while simultaneously blowing air-suspended cellulose fibers into the stream of meltblown fibers. The coform material may also include other materials, such as superabsorbent particles. The meltblown fibers containing wood fibers are collected on a forming surface, such as provided by a foraminous belt. The forming surface may include a gas-pervious material, such as spunbonded fabric material, that has been placed onto the forming surface.

"Compression" refers to the process or result of pressing by applying force on an object, thereby increasing the density of the object.

The term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, solvents, particulates and materials added to enhance processability of the composition.

Further, the diaper can comprise "containment flaps" or "barrier cuffs". The containment flaps are generally thought to be particularly well suited for the containment of fecal matter and to prevent the lateral flow of liquid waste until such time as the liquid waste can be absorbed by the absorbent article. Many constructions of containment flaps are known. Such containment flaps generally comprise a proximal edge, intended to be attached to the absorbent article, and an opposite distal edge which is generally not attached to the absorbent article along at least a portion of its length. An elastic member is generally located adjacent the distal edge to assist in maintaining the containment flap in an upright condition and in maintaining a sealing relationship between the distal edge of the containment flap and the body of a wearer during use. The elastic member is generally located between two layers of material so that the elastic does not come into contact with the body of a wearer. The containment flaps may be manufactured from a wide variety of materials such as polypropylene, polyester, rayon, nylon, foams, plastic films, formed films, and elastic foams. A number of manufacturing techniques may be used to manufacture the containment flaps. For example, the containment flaps may be woven, non-woven, spunbonded, carded, cast, blown or the like.

The diaper can comprise leg containment gaskets. Leg "containment gaskets" help prevent leakage of bodily exudates when the wearer exerts compressive forces on the absorbent article. In particular, the stiffness of the leg containment gaskets prevents twisting and bunching of the leg openings of the absorbent article which can lead to leaks. In addition, the elasticity and conformability of the leg containment gaskets ensures that the bodyfacing surface of the leg containment gaskets provides an adequate seal against the body of the wearer. The physical properties of the leg containment gaskets, such as the thickness and stiffness, also function to space the bodyside liner, outer cover and absorbent core away from the wearer's body when in use. As such, void volume is created between the wearer's body and the bodyside liner and absorbent core of the absorbent article to help contain body exudates.

"Continuous" means that the described structure is a closed-loop structure. The continuous structure may be unitary, i.e., a one-piece structure, or may be made up of individual elements suitably joined together to form a closed-loop.

A "continuous waistband" can be an elastomeric, cloth-like, nonwoven fibrous material, such as an elastomeric stretch bonded laminate web or an elastomeric meltblown web. By proper selection of materials, the continuous waistband can be rendered temporarily elastically inhibited, such as by compression. Once temporarily elastically inhibited, the elastic material, of which waistband is comprised, can be activated, such as by treating with heat, to recover to a state of elasticity.

"Conventional hot-melt adhesive" means a formulation that generally comprises several components. These components typically include one or more polymers to provide cohesive strength (e.g., aliphatic polyolefins such as poly (ethylene-co-propylene) copolymer; ethylene vinyl acetate copolymers; styrene-butadiene or styrene-isoprene block copolymers; etc.); a resin or analogous material (sometimes called a tackifier) to provide adhesive strength (e.g., hydrocarbons distilled from petroleum distillates; rosins and/or rosin esters; terpenes derived, for example, from wood or citrus, etc.); perhaps waxes, plasticizers or other materials to modify viscosity (i.e., flowability) (examples of such materials include, but are not limited to, mineral oil, polybutene, paraffin oils, ester oils, and the like); and/or other additives including, but not limited to, antioxidants or other stabilizers. A typical hot-melt adhesive formulation might contain from about 15 to about 35 weight percent cohesive strength polymer or polymers; from about 50 to about 65 weight percent resin or other tackifier or tackifiers; from more than zero to about 30 weight percent plasticizer or other viscosity modifier; and optionally less than about 1 weight percent stabilizer or other additive. It should be understood that other adhesive formulations comprising different weight percentages of these components are possible.

The term "density" or "concentration" when referring to the absorbent material, in particular the SAP, of a layer, refers to the amount of the absorbent material divided by the surface area of the layer over which the absorbent material is spread out.

As used herein, the term "diaper" refers to an absorbent article generally worn by incontinent persons about the lower torso.

"Discontinuous bonding pattern" as used herein refers to a pattern of bonding areas, in particular bonding areas between layers, whereby at least in at least one region the layers are not bonded. A discontinuous bonding pattern may comprise a connected bonding area or multiple disconnected bonding areas. A discontinuous bonding pattern further may comprise a connected bonding area comprising a number of holes, where the layers are not bonded, preferably according to a regular pattern, or it may comprise discrete disconnected bonding areas, e.g. a point bonded pattern which comprises a plurality of separate bonding points surrounded by unbonded areas or a line-bonded pattern which comprises a plurality of separate bonding lines alternated by unbonded areas, preferably according to a regular pattern.

"Disposable absorbent garments" preferably comprise a front section, a back section, a crotch section, elastic side sections, seams, a continuous waist opening, and/or a pair of continuous leg openings. Each elastic side section preferably comprises front elastic side member and a back elastic side member, which may be joined together at a respective seam.

The term "disposable" is used herein to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "elastic resistance" describes an elastic force that tends to resist an applied tensile force causing a material provided therewith to tend to contract to an untensioned configuration in response to a stretching force.

As used herein, the terms "elastic", "elastomeric", "elasticity" or derivations thereof are used to describe the ability of various materials and objects comprised of such to reversibly undergo deformation under stress, e.g., become stretched or extended, in at least one direction when a force is applied to the material and to resume substantially to their original dimensions upon relaxing, i.e., when the force is released, without rupture or breakage. Preferably, it refers to a material or composite which can be elongated in at least one direction by at least 50% of its relaxed length, i.e., elongated to at least 150% of its relaxed length, and which will recover upon release of the applied tension at least 40% of its elongation. Accordingly, upon release of the applied tension at 50% elongation, the material or composite contracts to a relaxed length of not more than 130% of its original length. Examples of suitable elastomer materials include polyether-polyamide block copolymers, polyurethanes, synthetic linear A-B-A and A-B block copolymers, chlorinated rubber/EVA (ethylene-vinyl acetate) blends, EPDM (ethylene-propylene diene monomer) rubbers, EPM (ethylene-propylene monomer) rubbers, blends of EPDM/EPM/EVA, and the like.

The term "elasticized" or "elastified" refers to a material, layer, or substrate that is naturally non-elastic, but which has been rendered elastic by, for example, suitably joining an elastic material, layer, or substrate thereto.

The term "contractibly connectable" or "contractibly affixed" refer to an elastic material which is adapted to be or is connected to another material, with the elastic material in its stretched state, which forces the contraction of said other material, once the elastic material is relaxed. As an example, an elastic material (elastic film or elastic strands) is stretched and then connected to and between two non-woven web materials. When the combination is relaxed both the elastic material and the non-woven material are contracted and give rise to wrinkles/crinkles.

"Elongation" means the ratio of the extension of a material to the length of the material prior to the extension (expressed in percent). "Extension" means the change in length of a material due to stretching (expressed in units of length).

As used herein the term "extensible" means elongatable in at least one direction, but not necessarily recoverable.

The term "fabrics" is used to refer to all of the woven, knitted and nonwoven fibrous webs.

The term "finished" or "final", when used with reference to a product, means that the product has been suitably manufactured for its intended purpose.

The term "flexible" refers to materials which are compliant and which will readily conform to the general shape and contours of the wearer's body.

As used herein, the term "garment" means any type of apparel which may be worn. This includes diapers, training pants, incontinence products, surgical gowns, industrial workwear and coveralls, undergarments, pants, shirts, jackets and the like.

The term "graphic" includes, but is not limited to, any type of design, image, mark, figure, codes, words, patterns, or the like. For a product such as a training pant, graphics will generally include objects associated with little boys and little girls, such as multi-color trucks, airplanes, balls, dolls, bows, or the like.

Many of the known superabsorbent polymer particles exhibit gel blocking. "Gel blocking" occurs when superabsorbent polymer particles are wetted and the particles swell so as to inhibit fluid transmission to other regions of the absorbent structure. Wetting of these other regions of the absorbent member therefore takes place via a very slow diffusion process. In practical terms, this means acquisition of fluids by the absorbent structure is much slower than the rate at which fluids are discharged, especially in gush situations. Leakage from the absorbent article can take place well before the particles of SAP in the absorbent member are even close to being fully saturated or before the fluid can diffuse or wick past the "blocking" particles into the rest of the absorbent member. Gel blocking can be a particularly acute problem if the superabsorbent polymer particles do not have adequate gel strength and deform or spread under stress once the particles swell with absorbed fluid.

The term "high-absorbency material" refers to materials that are capable of absorbing at least 10 times their own weight in liquid. The high-absorbency material may comprise absorbent gelling materials, such as superabsorbent polymers. Superabsorbent polymers are water-swellable, water-insoluble organic or inorganic materials capable of absorbing at least about 20 times their own weight of an aqueous solution containing 0.9 weight percent of sodium chloride. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces. Examples of synthetic absorbent gelling material polymers include the alkali metal and ammonium salts of poly(acrylic acid) and poly (methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be used. Synthetic absorbent gelling materials typically are xerogels which form hydrogels when wetted. The term "hydrogel", however, has commonly been used to also refer to both the wetted and unwetted forms of the material. The high-absorbency material may be in any of a wide variety of geometric forms. As a general rule, it is preferred that the high-absorbency material be in the form of discrete particles. However, the high-absorbency material may also be in the form of fibres, flakes, rods, spheres, needles, spiral or semi-spiral, cubic, rod-like, polyhedral, or the like. Conglomerates of particles of high-absorbency material may also be used. The high-absorbency material may be present in the absorbent core in an amount of from about 5 to about 100 weight percent and desirably from about 30 to about 100 weight percent based on the total weight of the absorbent core. The distribution of the high-absorbency material within the different portions of the absorbent core can vary depending upon the intended end use of the absorbent core. The high-absorbency material may be arranged in a generally discrete layer within the matrix of hydrophilic fibres. Alternatively, the absorbent core may comprise a laminate of fibrous webs and high-absorbency material or other suitable means of maintaining a high-absorbency material in a localized area.

"Hydroentanglement process" refers to the manufacturing of nonwoven webs. The process involves directing a series of water jets towards a fibrous web which is supported on a moving porous belt. The water jets pass downwards through the mass of fibres and on making contact with the surface of the belt, the jets rebound, and break up: the energy released causes entanglement of the mass of fibres.

The term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. The term "wettable" is meant to refer to a fiber which exhibits a liquid, such as water, synthetic urine, or a 0.9 weight percent aqueous saline solution, in air contact angle of less than 90°, whereas "hydrophobic" or "non-wettable" describes fibers having contact angles equal to or greater than 90°.

As used herein, the term "impermeable" generally refers to articles and/or elements that are substantially not penetrated by aqueous fluid through the entire thickness thereof under a pressure of 1.0 kPa or less. Preferably, the impermeable article or element is not penetrated by aqueous fluid under pressures of 3.4 kPa or less. More preferably, the impermeable article or element is not penetrated by fluid under pressures of 6.8 kPa or less. An article or element that is not impermeable is permeable.

"Integral" is used to refer to various portions of a single unitary element rather than separate structures bonded to or placed with or placed near one another.

"Join", "joining", "joined", or variations thereof, when used in describing the relationship between two or more elements, means that the elements can be connected together in any suitable manner, such as by heat sealing, ultrasonic bonding, thermal bonding, by adhesives, stitching, or the like. Further, the elements can be joined directly together, or may have one or more elements interposed between them, all of which are connected together.

The term "laid-flat state" or "fully stretched state" or "extended state" is intended to refer to the article when it is flattened into a plane or is substantially flattened into a plane and is used in contrast to when the article otherwise positioned, such as when the article is folded or shaped in or for use by a wearer (i.e. typically in a manner as illustrated in FIG. 1 to FIG. 5).

"Laminate" refers to elements being attached together in a layered arrangement.

The use of the term "layer" can refer, but is not limited, to any type of substrate, such as a woven web, nonwoven web, films, laminates, composites, elastomeric materials, or the like. A layer can be liquid and air permeable, permeable to air but impermeable to liquids, impermeable both to air and liquid, or the like. When used in the singular, it can have the dual meaning of a single element or a plurality of elements.

"Liquid" means a nongaseous substance and/or material that flows and can assume the interior shape of a container into which it is poured or placed.

"Longitudinal" is a direction running parallel to the maximum linear dimension of the article.

The term "meltblown fibers" means fibers formed by extruding a molten thermoplastic material through a plurality of fine, usually circular, die capillaries as molten threads or filaments into a high velocity gas stream (e.g. air) which attenuates the filaments of molten thermoplastic material to reduce their diameter, which may be to microfiber diameter. In general, meltblown fibers have an average fiber diameter of up to about 10 microns. After the fibers are formed, the meltblown fibers are carried by the high velocity gas stream and are deposited on a collecting surface to form a web of randomly disbursed meltblown fibers.

The term "nonelastic" or "inelastic" refers to any material which does not fall within the definition of "elastic" above, typically by not comprising elastic materials such as elastic web materials described herein.

The term "nonwoven fabric or web" means a sheet material having a structure of individual fibers or threads which are interlaid, but not in a regular manner such as occurs with knitting or weaving processes. Nonwoven fabrics or webs have been formed from many processes such as for example, meltblowing processes, spunbonding processes, and bonded carded web processes.

"Pant body" refers to a garment that has a waist opening and a pair of leg openings, similar to shorts, swim wear, or the like. The described garment may or may not have a manually tearable side seam.

By the terms "particle", "particles", "particulate", "particulates" and the like, it is meant that the material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

The term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

By the term "pre-packed" as used herein, is meant that one or more absorbent articles are packed in a single unit before being stacked.

"Pulp fluff" or "fluff pulp" refers to a material made up of cellulose fibers. The fibers can be either natural or synthetic, or a combination thereof. The material is typically lightweight and has absorbent properties.

The "retention portion" or "liquid absorption layer" is part of the absorbent medium (or core). This portion may comprise a matrix of hydrophilic fibers, such as a web of cellulosic fluff, mixed with particles of high-absorbency material. In particular arrangements, the retention portion may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness of the absorbent structure, with lower concentrations toward the bodyside of the absorbent structure and relatively higher concentrations toward the outerside of the absorbent structure. The superabsorbent particles may also be arranged in a generally discrete layer within the matrix of hydrophilic fibers. In addition, two or more different types of superabsorbent materials may be selectively positioned at different locations within or along the fiber matrix.

As used herein the term "sheet" or "sheet material" refers to woven materials, nonwoven webs, polymeric films, polymeric scrim-like materials, and polymeric foam sheeting.

The term "spunbond fibers" refers to fibers formed by extruding molten thermoplastic polymers as filaments or fibers from a plurality of relatively fine, usually circular, capillaries of a spinneret, and then rapidly drawing the extruded filaments by an eductive or other well-known drawing mechanism to impart molecular orientation and physical strength to the filaments. The average diameter of spunbond fibers is typically in the range of from 15-60 μm or higher. The spinneret can either be a large spinneret having several thousand holes per meter of width or be banks of smaller spinnerets, for example, containing as few as 40 holes.

The term "spunbond meltblown spunbond" (SMS) nonwoven fabric as used herein refers to a multi-layer composite sheet comprising a web of meltblown fibers sandwiched between and bonded to two spunbond layers. A SMS nonwoven fabric can be formed in-line by sequentially depositing a first layer of spunbond fibers, a layer of meltblown fibers, and a second layer of spunbond fibers on a moving porous collecting surface. The assembled layers can be bonded by passing them through a nip formed between two rolls that can be heated or unheated and smooth or patterned. Alternately, the individual spunbond and meltblown layers can be pre-formed and optionally bonded and collected individually such as by winding the fabrics on wind-up rolls. The individual layers can be assembled by layering at a later time and bonded together to form a SMS nonwoven fabric. Additional spunbond and/or meltblown layers can be incorporated in the SMS fabric, for example spunbond-meltblown-meltblown-spunbond (SMMS), etc.

"Staple fibers" refer to commercially available fibers having diameters ranging from less than about 0.001 mm to more than about 0.2 mm; they come in several different forms such as short fibers ranging from about 10 to 50 mm in length and long fibers with a length higher than 50 mm, preferably up to 100 mm.

By "stretch", it is meant that the material has the ability to extend beyond its original size in at least one dimension when subjected to a tensile force (i. e., tension) applied in the direction of that dimension, without breaking the material. An extension of for example 50% means that the material with an initial length of 100 mm has reached a length of 150 mm. "Stretch" may be unidirectional, bi-directional, or multi-directional. The specific "stretch" properties of a material may vary along any of the stretch vectors. The term can include elastic materials, as well as nonwovens that can be inherently extensible, but not necessarily in an elastic manner. Such nonwovens can be made to behave in an elastic manner by bonding them to elastic films.

Use of the term "substrate" includes, but is not limited to, woven or nonwoven webs, porous films, ink permeable films, paper, composite structures, or the like.

Superabsorbent materials suitable for use in the present invention are known to those skilled in the art, and may be in any operative form, such as particulate form, fibers and mixtures thereof. Generally stated, the "superabsorbent material" can be a water-swellable, generally water-insoluble, hydrogel-forming polymeric absorbent material, which is capable of absorbing at least about 15, suitably about 30, and possibly about 60 times or more its weight in physiological saline (e.g. saline with 0.9 wt % NaCl). The superabsorbent material may be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. The superabsorbent material may suitably be included in an appointed storage or retention portion of the absorbent system, and may optionally be employed in other components or portions of the absorbent article. The superabsorbent material may be included in the absorbent layer or other fluid storage layer of the absorbent article of the present invention in an amount up to about 60% by weight. Typically, the superabsorbent material, when present, will be included in an amount of about 5% to about 40% by weight, based on the total weight of the absorbent layer.

"Superabsorbent polymer particles" or "SAPs" refer to water-swellable, water-insoluble organic or inorganic materials capable, under the most favorable conditions, of absorbing at least about 10 times their weight, or at least about 15 times their weight, or at least about 25 times their weight in an aqueous solution containing 0.9 weight percent sodium chloride. In absorbent articles, such as diapers, incontinent diapers, etc., the particle size is typically ranging between 100 to 800 μm, preferably between 300 to 600 μm, more preferably between 400 to 500 μm.

"Tension" includes a uniaxial force tending to cause the extension of a body or the balancing force within that body resisting the extension.

As used herein, the term "thermoplastic" is meant to describe a material that softens when exposed to heat and which substantially returns to its original condition when cooled to room temperature.

The term "top sheet" refers to a liquid permeable material sheet forming the inner cover of the absorbent article and which in use is placed in direct contact with the skin of the wearer. The top sheet is typically employed to help isolate the wearer's skin from liquids held in the absorbent structure. The top sheet can comprise a nonwoven material, e.g. spunbond, meltblown, carded, hydroentangled, wetlaid etc. Suitable nonwoven materials can be composed of man-made fibres, such as polyester, polyethylene, polypropylene, viscose, rayon etc. or natural fibers, such as wood pulp or cotton fibres, or from a mixture of natural and man-made fibres. The top sheet material may further be composed of two fibres, which may be bonded to each other in a bonding pattern. Further examples of top sheet materials are porous foams, apertured plastic films, laminates of nonwoven materials and apertured plastic films etc. The materials suited as top sheet materials should be soft and non-irritating to the skin and be readily penetrated by body fluid, e.g. urine or menstrual fluid. The inner coversheet may further be different in different parts of the absorbent article. The top sheet fabrics may be composed of a substantially hydrophobic material, and the hydrophobic material may optionally be treated with a surfactant or otherwise processed to impart a desired level of wettability and hydrophilicity.

As used herein, the term "transverse" or "lateral" refers to a line, axis, or direction which lies within the plane of the absorbent article and is generally perpendicular to the longitudinal direction.

"Ultrasonic welding" refers to a technology which joins two materials by melting them with heat generated from ultrasonic oscillation and then laminating them together, such that the molten materials flow and fill the gap between the two unaffected portions of the two materials, respectively. Upon cooling and shaping, the two materials are joined together.

As used herein, the term "water-swellable, water-insoluble" is meant to refer to a material that, when exposed to an excess of water, swells to its equilibrium volume but does not dissolve into the solution. As such, a water-swellable, water-insoluble material generally retains its original identity or physical structure, but in a highly expanded state, during the absorption of the water and, thus, must have sufficient physical integrity to resist flow and fusion with neighboring particles.

The term "proximal" as used herein has its common meaning, i.e. situated close to, proximate, next to, nearest to, adjacent, bordering, contiguous. The term "distal" as used herein has its common meaning, i.e. situated away from, farthest from.

Embodiments of the articles according to the disclosure will now be described. It is understood that technical features described in one or more embodiments maybe combined with one or more other embodiments without departing from the intention of the disclosure and without generalization therefrom.

Figure 1:
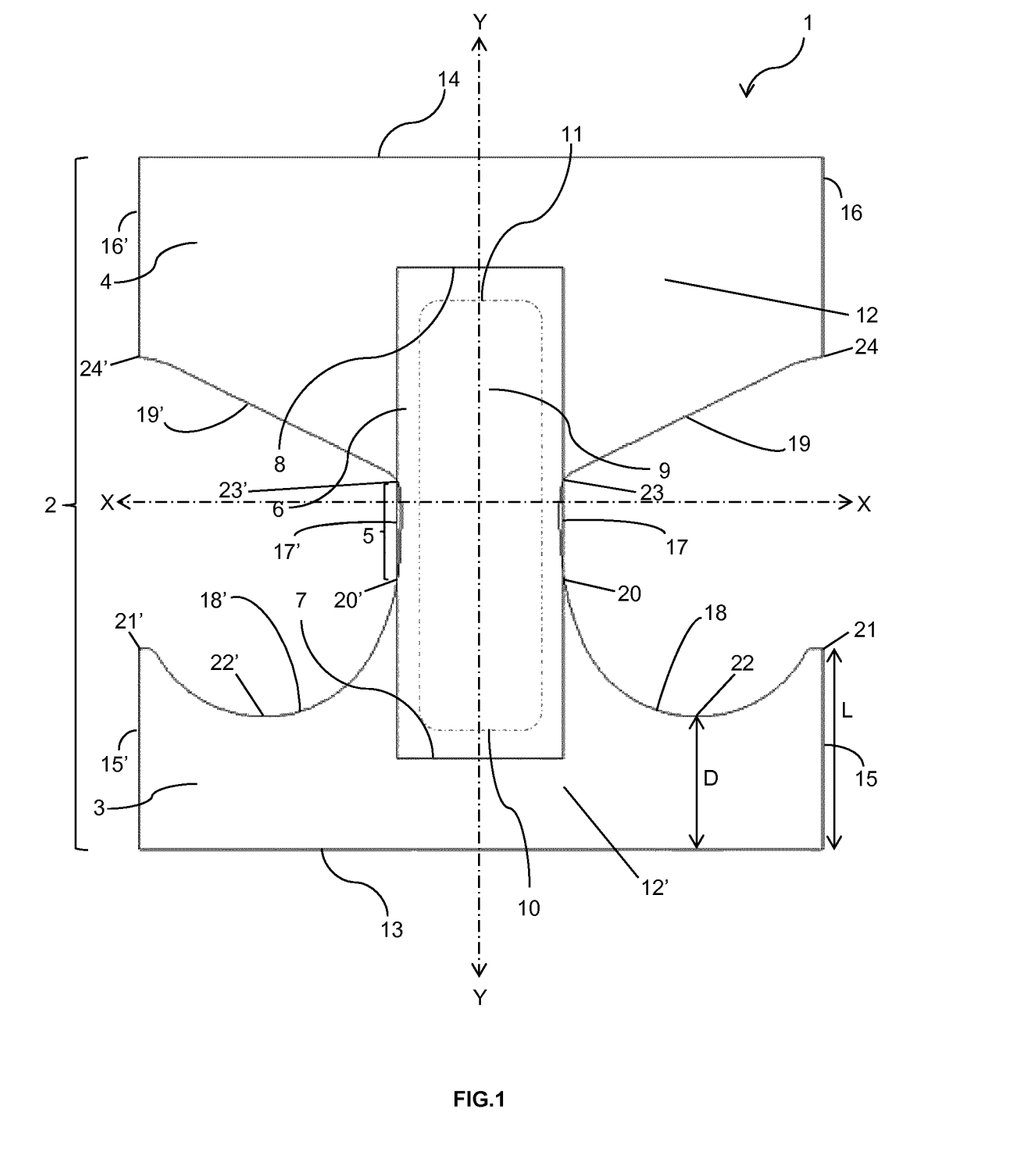
FIG. 1 is a schematic plan view of an unassembled and fully stretched article according to an embodiment of the present disclosure.
Figure 2:
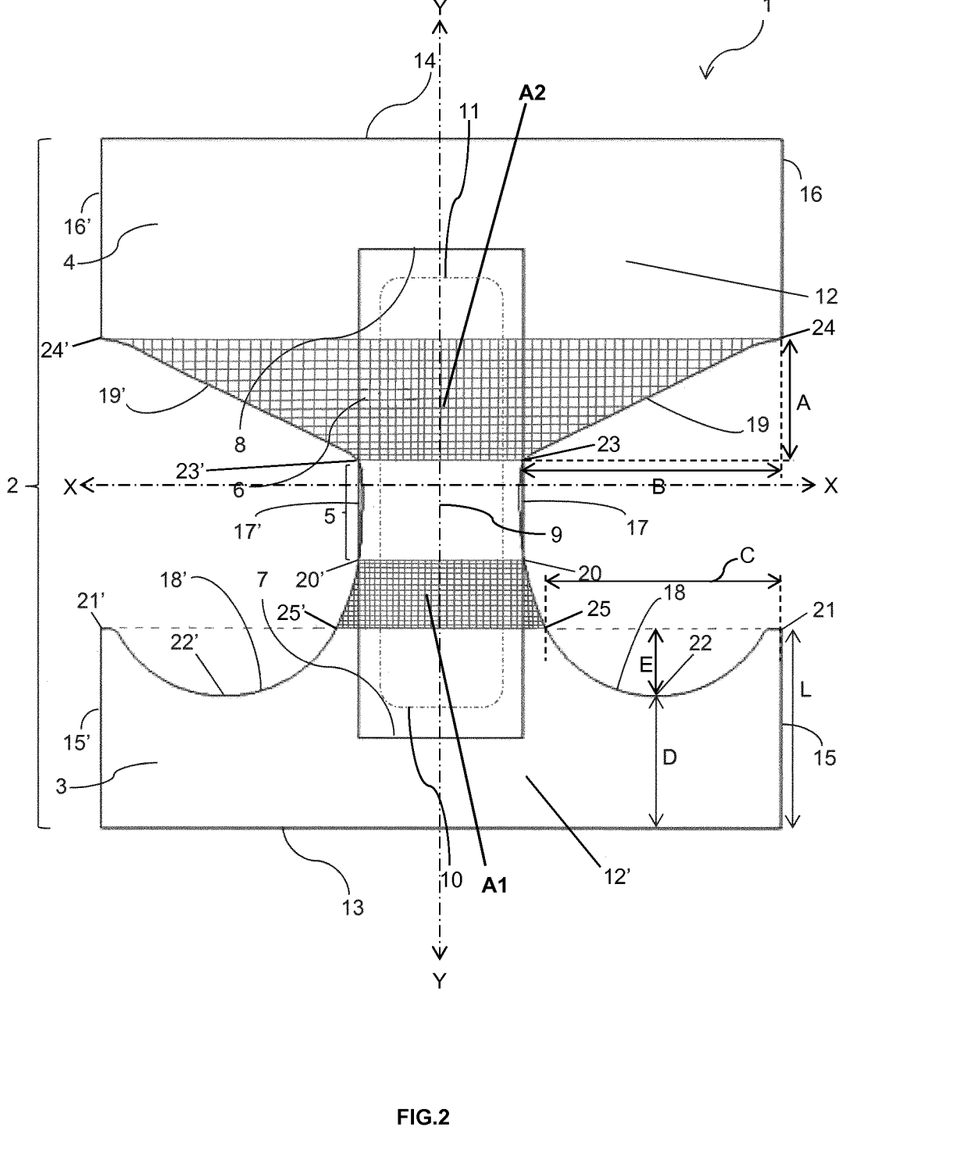
FIG. 2 is a schematic plan view of an unassembled and fully stretched article according to an embodiment of the present disclosure.

In a first aspect and with reference to FIGS. 1 and 2, the disclosure herein relates to an absorbent article 1, preferably an incontinence diaper, more preferably an incontinence pant-like diaper, having a longitudinal axis Y-Y and a transverse axis X-X, comprising: a chassis 2 including a skin-facing side, a garment-facing side opposite to the skin-facing side, a front waist region 3, a back waist region 4 and a crotch region 5 extending between said front and back waist regions 3,4; a liquid-absorbent member 6 having front and back ends 7,8 extending across the crotch region 5 into the front and back waist regions 3,4, the liquid-absorbent member including a liquid-absorbing core 9, the liquid-absorbing core 9 having front and back ends 10,11; and an elastic web material 12 contractibly connectable to at least the back waist regions 4 under tension in the transverse axis X-X, wherein the front and back waist regions 3,4 comprise front and back waist ends 13,14 and front and back waist lateral edges 15,15',16,16' extending along a direction parallel to the longitudinal axis Y-Y and wherein, when the front and back waist regions 3,4 are joined, preferably along front and back waist lateral edges, a waist-opening is formed by the front and back waist ends 13,14 and a pair of leg-openings are formed by one or more crotch-leg-peripheral-edges 17,17' and front and back waist-leg-peripheral-edges 18,18',19,19', and wherein first and second front waist-leg-peripheral-edges 18,18' extend from a first position 20,20' proximal to the crotch region 5 to a second position 21,21' distal therefrom and proximal to a front waist lateral edge 15,15', said first and second front waist-leg-peripheral-edges 18,18' being oppositely disposed from the longitudinal axis Y-Y and wherein first and second back waist-leg-peripheral-edges 19,19' extend from a third position 23,23' proximal to the crotch region 5 to a fourth position 24,24' distal therefrom and proximal to a back waist lateral edge 16, 16', said first and second back waist-leg-peripheral-edges 19,19' being oppositely disposed from the longitudinal axis Y-Y. It is characterized in that distance D, extending parallel to the longitudinal axis Y-Y between the front waist end 13 and a fifth position 22,22' along the first and second front waist-leg-peripheral-edges 18,18' which is closest to the front waist end 13, is smaller than length L of a front waist lateral edge 15,15' extending parallel to the longitudinal axis Y-Y.

It has been found that creating such a negative geometry, i.e. void forms, in the front waist region provides an improved snug fit in particular in the groin region of the wearer: less creases are created, which improves comfort and which minimizes viewability of the product through the clothes of the wearer. In addition the reduction of creases through which the liquid may flow reduces the risk of leakage.

The present invention is suitable for open diapers, wherein the front and back waist regions 3,4 may be joined for example with tapes or hook-and-loop fasteners. The present invention is particularly suitable for pant-like diapers wherein the front and back waist regions 3,4 may be joined along front and back waist lateral edges, for example via seams.

Otherwise defined, the first position 20,20' and the third position 23,23' are situated at the spots where the leg peripheral edges 17,17',18,18',19,19' defining the leg openings "cross" the liquid absorbent member 6. Generally, these positions correspond the points at which the angle of the edge of the leg opening changes most abruptly (i.e. the point at which the rate of change of the angle of the edge of the leg opening with respect to the transverse direction is highest). The crotch region 5 is then defined as the region included within the first position 20,20' and the third position 23,23'.

The absorbent article of the invention also comprises an elastic web material 12' contractibly connectable to the front waist region 3 under tension in the transverse axis X-X. This may allow the article to snugly conform to the anatomy of the wearer's belly.

In a preferred embodiment, each of the first and second front waist-leg-peripheral-edges 18,18' extend in an inward curved, i.e. concave, manner along opposite directions from the longitudinal axis Y-Y. This may further improve the snug fit in the groin region of the wearer.

Preferably the ratio of distance D to length L is at least 30% or at least 35%, more preferably at least 40% or at least 45%, still more preferably at least 50% or at least 55%. It is preferably at most 95% or at most 90%, more preferably at most 85% or at most 80%, still more preferably at most 75% or at most 70%. D/L is preferably within the range 45% to 80%, more preferably within the range 50% to 75%, still more preferably within the range 55% to 70%. We have indeed found that if the negative geometry is too deep, i.e. D is too short compared to L, the article may become uncomfortable to wear and/or the elastic web material 12' may lose tension, thereby creating unacceptable shirring. In addition, it might have a negative impact on the fit at the back of the absorbent article.

A sixth position 25,25' is defined along the first and second front waist-leg-peripheral-edges 18,18', which is proximal to the crotch region 5 and at a distance of the front waist end 13 parallel to the longitudinal axis Y-Y equal to L. The negative geometry may then further be defined by a ratio E versus C, where C is defined as the opening of the negative geometry, at a distance L of the front waist end 13, i.e. the distance extending parallel to the transverse axis X-X between the sixth position 25,25' and the second position 21,21' and E is defined as the depth of the negative geometry, extending parallel to the longitudinal axis Y-Y, such as E equals to L minus D. Such a ratio E/C is preferably at least 10% or at least 12%, more preferably at least 15% or at least 20%. It is preferably at most 40% or at most 35%, more preferably at most 30%. E/C is preferably within the range 10% to 35%, more preferably within the range 12% to 32%, even more preferably within the range 15% to 32%. We have indeed found that, at equivalent D/L ratio, if the first position 20,20' is closer to the front waist end 13, i.e. C is longer, some people may experience less comfort and fit. For the same reason and to minimize leakage, preferably the distance extending parallel to the longitudinal axis Y-Y between the first position 20,20' and the front waist end 13 is greater than L.

Preferably the article is free from an elastic thread proximal and substantially parallel to the first and second front waist-leg-peripheral-edges 18,18', to avoid shirring. The negative geometry is rather to be seen as an interruption into the continuity of the elastic web material 12'.

It might be advantageous to ensure that a portion of the first and second front waist-leg-peripheral-edges 18,18' proximal to the front waist lateral edges 15,15' be substantially parallel to the front waist end 13. By "substantially parallel" here, we mean either strictly parallel, or with a deviation from the strict parallel which is at most 5°, preferably at most 3°. This portion may have a length substantially parallel to the front waist end which is at least 5 mm, preferably at least 7 mm, and/or at most 15 mm, preferably at most 13 mm, as measured along the transverse axis (X-X). This length may preferably depend on the size of the absorbent article, and in particular the ratio between the length of the portion substantially parallel to the front waist end and the length of the front waist end, both measured along the transverse axis (X-X) is preferably within the range 1.20 to 1.80, or within the range 1.30 to 1.70, more preferably within the range 1.35 to 1.65. This may help during the manufacturing process, when the articles are still in the form of a continuous ribbon of products, to ensure the solidity between two successively attached absorbent articles, before the cutting step into individual pieces.

A first area A1 (gridded in FIG. 2) is defined between the first and second front waist-leg-peripheral-edges 18,18', between the first and sixth positions 20,20',25,25'; and a second area A2 (gridded in FIG. 2) is defined between the first and second back waist-leg-peripheral-edges 19,19', between the third and fourth positions 23,23',24,24'.

In the present invention, at least 50% of the total surface area of the chassis 2 comprises said elastic web material 12,12', each of the first and second areas A1, A2 are substantially elastified, and the surface area of the elastified first area A1 is from 3% to 35%, preferably 3% to 30%, more preferably 3% to 25%, still more preferably 3% to 20%, of the surface area of the elastified second area A2, as measured in an extended state. Elasticizing substantially the entire region between opposing waist-leg-peripheral-edges may provide an improved snug fit in the transition area crotch to leg-opening-sides which minimizes its viewability through the clothes of a subject. However, in doing so, the risk of leakage from the lateral sides may be exacerbated, particularly in case of crease formation through which the liquid may flow. By ensuring that the surface area A1 is sufficiently small compared to A2 such crease formation may be limited, however if A1 is too small the loose regions formed due to disproportionate tension front-to-back result in greater exposure to leakage, it is thus desirable to size areas A1 and A2 as described herein. For avoidance of doubt, the term "surface area" as used herein is the surface area taken about a flat plane coinciding (or formed by) the longitudinal axis Y-Y and the transverse axis X-X with the article laid out flat (or in extended state) as shown in the figures herein.

In an embodiment, the surface area of the elastified first area A1 is from 5% to 18%, preferably from 7% to 15%, more preferably between 8% and 15%, of the surface area of the elastified second area A2, as measured in an extended state.

In a highly preferred embodiment, at least 70%, preferably at least 80%, more preferably between 83% and 99%, of the total surface area of the chassis 2 comprises the elastic web material 12,12'. An advantage of this arrangement being that a fit more similar to underwear is achieved, as well as better adherence to the body.

In an embodiment, the first and second areas A1, A2 comprise the elastic web material 12,12', said material 12,12' being arranged to provide elasticity to said first and second areas A1, A2.

In a preferred embodiment, each of the first and second back waist-leg-peripheral-edges 19,19' extend substantially obliquely and along opposite directions from the longitudinal axis Y-Y, and preferably in a substantially linear and/or curved manner, such that the third position 23,23' and the fourth position 24,24' are separated along a first distance A extending parallel to the longitudinal axis Y-Y, and further separated along a second distance B extending perpendicular to the longitudinal axis Y-Y and parallel to the transverse axis X-X, and wherein the distance ratio A/B is greater than 0.5, preferably between 0.5 and 0.8, more preferably between 0.5 and 0.7, even more preferably between 0.5 and 0.65. Such specific leg cut may influence not only the comfort but also the risk of leakage. By ensuring that in particular the leg cut on the back portion is within the identified ranges, the risk of creases forming at the back may be reduced and leakage prevention improved.

In an embodiment, the article has a front half defined by the edges of the article and a transverse centre line X-X of the article, and a rear half defined by the edges of the article and a transverse centre line X-X of the article, and a surface area of the front half is preferably within the range 60 to 90%, more preferably within the range 70 to 90%, still more preferably within the range 70 to 80% of a surface area of the rear half, as measured in an extended state of the article. This may provide a more pant-like shape of the absorbent article.

In a further embodiment, the article has a maximum width in the transverse direction and a maximum length in the longitudinal direction, and the ratio of the maximum width to the maximum length of the article is between 80% and 120%, preferably between 90% and 115% as measured in an extended state of the article. According to a preferred embodiment, the ratio of the distance extending parallel to the longitudinal axis Y-Y between the first position 20,20' and the front waist end 13 to the maximum width of the article is between 25% and 50%, preferably between 35% and 45%, as measured in an extended state of the article. Articles conforming to these measurements may provide a more pant-like shape of the absorbent article and a more secure fit.

In an embodiment, the liquid-absorbing core 9 extends over the one or more elastified materials 12,12' along the longitudinal axis Y-Y and both front and back ends 10,11 of the core 9 are disposed in the first and second areas A1, A2 respectively such that at least 40%, preferably between 40% and 75%, of the total surface area of said liquid-absorbing core 9 is comprised within the elastified first and second areas A1, A2. An advantage of this arrangement is to provide a snug fitting core without it bulging out, thus providing a discrete profile that comfortably adheres to the wearer's body.

In an embodiment, the first and second areas A1, A2 comprise the elastic web material 12,12' arranged to provide an elongation of from 200 to 300%, measured according to the method described herein. It has been found that if the elastic web material 12,12' has an elongation below 200%, the resulting substrate is too loose which in turn leads to increase risk of leakage, on the other hand if the elongation is above 300%, the substrate becomes too tight and thus limiting freedom of movement and increasing the risk of skin irritation.

In an embodiment, the first and second areas A1,A2 each have a total elastified surface corresponding to greater than 80%, preferably greater than 85%, more preferably from 90% to 99%, of the total surface area of the first and second areas A1,A2. An advantage of this embodiment is to ensure the product is effectively following/adapting to the curves of the subject.

As every individual may have a different shape, it is highly advantageous for the article to be capable of adapting itself accordingly.

In an embodiment, the elastic web material 12,12' is selected from the group consisting of an elastic film, elastic fibers, elastic strings, elastic networks, elastic nonwovens, and combinations thereof. Examples of suitable elastic networks are in the form of elastic extruded square netting provided such as those manufactured by Conwed® global netting solutions.

Preferably, the elastic web material 12,12' comprises a breathable elastic laminate preferably comprising an elastic film interposed between two elastic or inelastic nonwoven substrates. In this embodiment, the elastic web material 12,12' may be made breathable during the joining process by for example ultrasonic bonding to the respective sections of the chassis 2. An advantage of this arrangement is that microapertures are formed through the elastic web material 12,12' during the joining process without any particular post or pre-treatment needed.

The elastic laminate may comprise first and second layers of fibrous material and an elastic film layer disposed between the first and second fibrous layers, the fibrous layers may be in the form of nonwoven layers. Alternatively, similar elastic laminates may be made by laminating at least two nonwoven layers together, wherein at least one of the two nonwoven layers comprises an elastic nonwoven. This arrangement allows for a more premium feel and brings the subject experience closer to traditional underwear, not only the look, but also the touch and behaviour.

The elastic laminate may have a Water Vapour Transmission Rate according to ASTM E96-00 Procedure D of at least 1800 or 1900 g/m$^2$, preferably at least 2000 or 2500 g/m$^2$, more preferably at least 3000 g/m$^2$, even more preferably from 3200 to 5000 g/m$^2$, per 24 h.

In an embodiment, the portion of the crotch region between the first and second areas A1,A2 comprise one or more nonelastic materials (such as one or more nonwovens as described above), typically arranged such that said region is substantially inelastic (i.e. typically free of elastic web material such as elastic films and the like). An advantage of this arrangement is a reduction in cost in that an elastic material in this particular region can be omitted as it is believed not to negatively impact the comfort and leakage prevention, so long as the elastic web material is present in the leg regions as described in the preceding embodiments. Moreover, without wishing to be bound by theory it is believed that if this region was elastified (i.e. a continuous elastified surface from front to back waist regions), a greater risk of wrinkle formation would result, such leading to undesirable skin irritation, discomfort, as well as unpleasant aesthetic appearance. It is thus desirable that a portion of the crotch region 5 between the first and second areas A1,A2 remain inelastic such to provide a discontinuous elasticity between the front waist region 3 and the back waist region 4.

In an embodiment, at least one of the elastic web materials continuously extends between opposing lateral edges 15,15', 16,16' of each of the front and back waist regions 3,4. By ensuring that at least one of the elastics on each front/back region is not deactivated, a better overall elastization and fit is achieved.

In a preferred embodiment (not shown), at least the front waist region 3 comprises a series and/or pattern of continuous or discontinuous bonds arranged to provide at least one further region having an elongation that is different from the elongation of neighboring portions of said front waist region 3. More preferably, the continuous or discontinuous bonds are arranged such to substantially circumscribe at least one of the further regions, preferably located at a position proximal to the crotch region 5, and arranged to reduce the elasticisation within said substantially circumscribed further region, preferably forming a pocket having a lower elongation than the elongation of neighboring surfaces outside said substantially circumscribed further region. This embodiment is particularly advantageous for providing better underwear-like fit, particularly for male subjects.

In an embodiment, the absorbent core may comprise superabsorbent polymer (typically in the form of particles) and/or cellulosic fibers (or fluff). Due to the high concentrations of superabsorbent particles, or other high-absorbency material, in the retention portion (i.e. the portion whithin the crotch region exposed to the larges flow of exudates), there can be an increased difficulty with regard to containing the high-absorbency particles within the retention portion and restricting the movement or migration of the superabsorbent onto the bodyside of the pants. To improve the containment of the high-absorbency material, the absorbent structure can include an improved overwrap, such as a wrap sheet, placed immediately adjacent and around the retention portion. The wrap sheet is preferably a layer of absorbent material which covers the major bodyside and outerside surfaces of the retention portion, and preferably encloses substantially all of the peripheral edges of the retention portion to form a substantially complete envelope thereabout. Alternatively, the wrap sheet can provide an absorbent wrap which covers the major bodyside and outerside surfaces of the retention portion, and encloses substantially only the lateral side edges of the retention portion. Accordingly, both the linear and the inwardly curved portions of the lateral side edges of the wrap sheet would be closed about the retention portion. In such an arrangement, however, the end edges of the wrap sheet may not be completely closed around the end edges of the retention portion at the waistband regions of the article. The wrap sheet may comprise a multi-element wrapsheet which includes a separate bodyside wrap layer and a separate outerside wrap layer, each of which extends past all or some of the peripheral edges of the retention portion. Such a configuration of the wrap sheet can, for example, facilitate the formation of a substantially complete sealing and closure around the peripheral edges of the retention portion. The bodyside and outerside layers of the wrap sheet may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials (for example may comprise a meltblown web composed of meltblown polypropylene fibers or low porosity cellulosic tissue web composed of a blend of hardwood/softwood fibers) which has a relatively low porosity. The low porosity bodyside layer can better prevent the migration of superabsorbent particles onto the wearer's skin, and the high porosity, lower basis weight outerside layer can help reduce costs.

In an embodiment (not shown), the crotch portion of the absorbent article preferably comprises opposite longitudinal side portions which comprise a pair of elasticized, longitudinally-extending "leg cuffs". The leg cuffs are generally adapted to fit about the legs of a wearer when in use and serve as a mechanical barrier to the lateral flow of body exudates. Leg cuffs are elasticized by leg elastics. The diaper further can comprise a front waist elastic and a rear waist elastic. Materials suitable for use in forming leg elastics are known to those skilled in the art. Exemplary of such materials are strands or ribbons of a polymeric, elastomeric material which are adhered to the diaper at the leg cuff while in a stretched position, or which are attached to the diaper while the diaper is pleated, such that elastic constrictive forces are imparted to the leg cuff. Examples of suitable elastomer materials that can be used include polyether-polyamide block copolymers, polyurethanes, synthetic linear A-B-A and A-B block copolymers, chlorinated rubber/EVA (ethylene-vinyl acetate) blends, EPDM (ethylene-propylene diene monomer) rubbers, EPM (ethylene-propylene monomer) rubbers, blends of EPDM/EPM/EVA, and the like.

Method of Measuring Elongation

This test method is designed to determine the elasticity of elastic web materials in incontinence pants to ensure usability of the pants. The pants are placed in a mounting frame and at predefined forces the percentage of elongation is determined.

Material: Tensile tester [like a Zwick/Roell Z1.0] with constant rate of extension calibrated according to the manufacturer's instructions; Clamps and jaws: each jaw face shall be smooth, flat and with a metallic surface and dimension of 30×60 mm. The faces shall be parallel and have matching centres with respect to one another in the same clamp and to the corresponding jaw face of the other clamp; Mounting frame: includes a top & bottom device to be placed between the clamps.

Procedure: The pants are placed over a mounting frame on the tensile testing machine and pulled with constant rate of extension. Values for elongation of the test products are obtained from a computer interface.

Definitions: Elongation: the deformation in the direction of load caused by a tensile force. Elongation is generally expressed as a percentage of the length of the stretched material to the length of the un-stretched material (=distance between frame-ends at the beginning of the test–LE); Extension: the change of length of a material due to stretching.

Equipment verification: Verify load cell: a calibrated verification weight of 500 g should give a force of 4.90(5) N±0.10 N.

Equipment Parameters: Following parameters are programmed: Pre-load: 0.1N; Cross Head Speed: 300 mm/min; End of Test: 22N Gage Length LE (mm) needs to be adjusted depending on the waist size of the pants: Small 220; Medium 250; Large 250; X-Large 270

Procedure: Assemble the mounting frame & zero the load cell; Adjust the gage length according to the waist size; Carefully slide the pant over the mounting frame; Zero the load cell; Start the test Force (N) and test path (mm) measurements will be recorded until 22N force is reached; Repeat for at least 5 products.

Calculation: Record the elongation value at standard setting forces 2N and 20N for each product. Measure the increase in length from the start of the force-extension curve to the point corresponding with the predefined force. Calculate the elongation as the percentage increase in length based on the gage length for both 2N and 20N.

EXAMPLES

Example 1

Four identical pant samples are made with varying dimensions in terms of (i) D/L ratio, and further (ii) E/C ratio. The samples are handed out in random order to a group of panelists (at least 3). The panelists are instructed to wear the samples and score each of them from a scale of from poor to excellent both in terms of fit and comfort. Results are recorded. Table 1 summarises the results with the % of panelists providing each of the indicated scoring.

TABLE 1 impact of D/L and E/C ratios on fit and comfort

| Sample | D/L (%) | E/C (%) | Poor (% of panelists) | Sufficient (% of panelists) | Good (% of panelists) | Excellent (% of panelists) |
|---|---|---|---|---|---|---|
| 1 | 66 | 28.6 | — | — | 17% | 83% |
| 2 | 66 | 26.6 | — | 8% | 75% | 17% |
| 3 | 100 | — | — | 92% | 8% | — |
| 4 | 34 | 54.4 | 100% | — | — | — |

Sample 3 is a pant according to European patent application EP17159249.6 filed on 3 Mar. 2017. It does not show a negative geometry as per the present invention.

Figure 3:
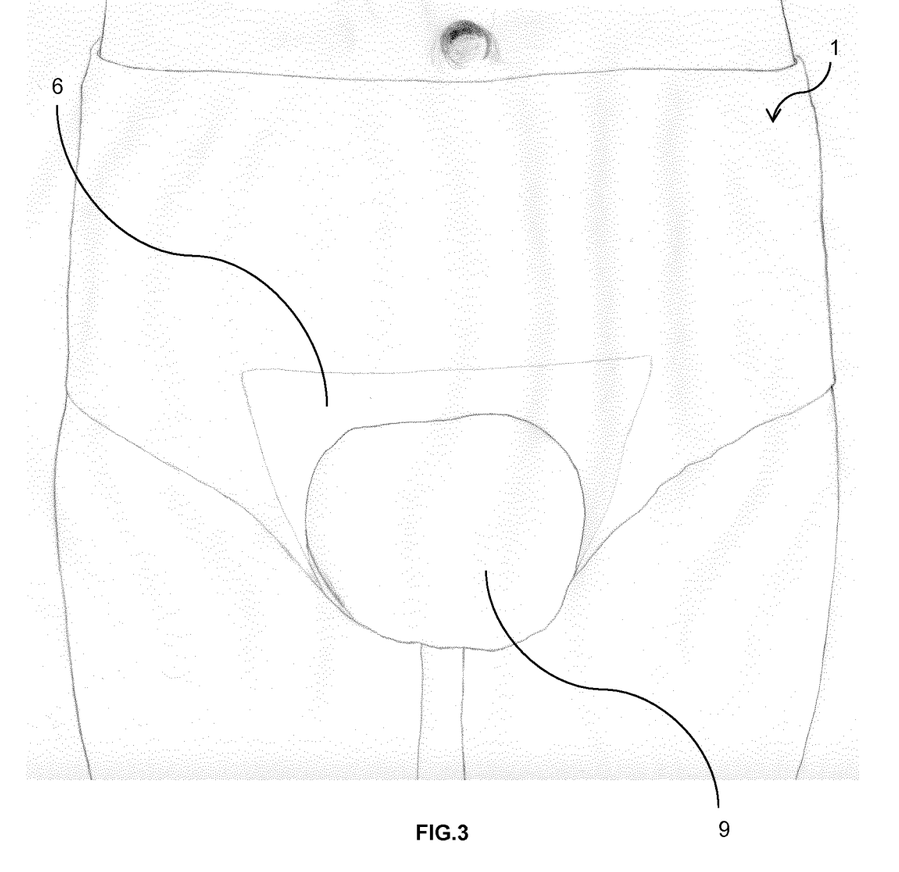
FIG. 3 is a front view of an article according to the invention, positioned on a mannequin.
Figure 4:
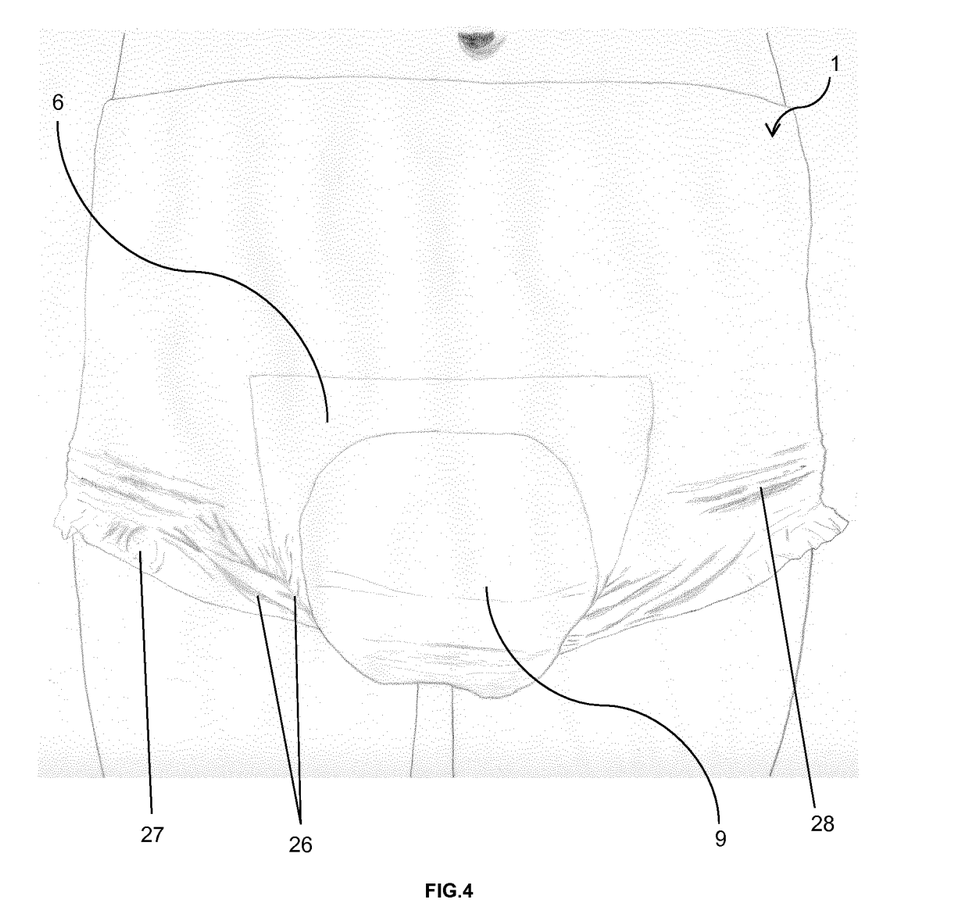
FIG. 4 is a front view of an article which is not in accordance with the present invention, positioned on a mannequin.

FIGS. 3 and 4 are front views of respectively sample 1 and sample 3, positioned on a mannequin. FIG. 3 clearly shows the perfect fit of the article in the front part of the mannequin, in particular in the groin region, where no crease or shirring is visible. It also shows the snug fit of the whole article to the body. FIG. 4, on the contrary, shows creases (26) in the groin region, shirring (27) on the frontal part of the leg, and folding creating an elongated protuberance (28) a few centimeters above the leg opening. Sample 3 is following the buttock folds, whilst sample 1 is furthermore following the groin. This latter shape may additionally release the pressure on the thigh, avoiding skin marks.

Example 2

Seven identical pant samples are made with varying dimensions in terms of (i) D/L ratio, and further (ii) E/C ratio. The A1/A2 ratio was kept around 6% for all samples B to G, and was around 8% for sample A. The samples are handed out in random order to a group of panelists (at least 3). The panelists are instructed to wear the samples and score each of them from a scale of from worst (=1) to best (=7) both in terms of fit and comfort. Results are recorded. Table 2 summarises the results with the % of panelists providing each of the indicated scoring.

TABLE 2 impact of D/L and E/C ratios on fit and comfort

| | D/L | E/C | % of panelists | | | | | | |
|---|---|---|---|---|---|---|---|---|---|
| Sample | (%) | (%) | Worst = 1 | 2 | 3 | 4 | 5 | 6 | Best = 7 |
| A | 100 | — | | | 50% | 33% | 17% | | |
| B | 94 | 5 | | | 17% | 50% | 33% | | |
| C | 82 | 15 | | | | | 17% | 83% | |
| D | 71 | 25 | | | | 16.5% | | 16.5% | 67% |
| E | 65 | 30 | | | 17% | | 50% | | 33% |
| F | 59 | 35 | | 83% | 17% | | | | |
| G | 47 | 45 | 100% | | | | | | |

Sample A is a pant according to European patent application EP17159249.6 filed on 3 Mar. 2017. It does not show a negative geometry as per the present invention.

This second panel test shows a clear preference from the panelists for the samples with E/C ratios of 15, 25 or 30%.

It is supposed that the present invention is not restricted to any form of realization described previously and that some modifications can be added to the presented example of fabrication without reappraisal of the appended claims.

The invention claimed is:

1. An absorbent article (1) having a longitudinal axis (Y-Y) and a transverse axis (X-X), comprising:
   a chassis (2) including a skin-facing side, a garment-facing side opposite to the skin-facing side, a front waist region (3), a back waist region (4) and a crotch region (5) extending between said front and back waist regions (3,4);
   a liquid-absorbent member (6) having front and back ends (7,8) extending across the crotch region (5) into the front and back waist regions (3,4), the liquid-absorbent member including a liquid-absorbing core (9), the liquid-absorbing core (9) having front and back ends (10,11); and
   an elastic web material (12,12') contractibly connectable to at least each of the front and back waist regions (3,4) under tension in the transverse axis (X-X),
   wherein the front and back waist regions (3,4) comprise front and back waist ends (13,14) and front and back waist lateral edges (15,15',16,16') extending along a direction parallel to the longitudinal axis (Y-Y) and wherein, when the front and back waist regions (3,4) are joined a waist-opening is formed by the front and back waist ends (13,14) and a pair of leg-openings are formed by one or more crotch-leg-peripheral-edges (17,17') and front and back waist-leg-peripheral-edges (18,18',19,19'),
   wherein first and second front waist-leg-peripheral-edges (18,18') extend from a first position (20,20') proximal to the crotch region (5) to a second position (21,21') distal therefrom and proximal to a front waist lateral edge (15,15'), said first and second front waist-leg-peripheral-edges (18,18') being oppositely disposed from the longitudinal axis (Y-Y) and wherein first and second back waist-leg-peripheral-edges (19,19') extend from a third position (23,23') proximal to the crotch region (5) to a fourth position (24,24') distal therefrom and proximal to a back waist lateral edge (16,16'), said first and second back waist-leg-peripheral-edges (19,19') being oppositely disposed from the longitudinal axis (Y-Y), wherein a fifth position (22,22') is defined along the first and second front waist-leg-peripheral-edges (18,18') which is closest to the front waist end (13), wherein a sixth position (25,25') is defined along the first and second front waist-leg-peripheral-edges (18,18') which is proximal to the crotch region (5) and at a distance of the front waist end (13) parallel to the longitudinal axis (Y-Y) equal to a length L, wherein a first area (A1) is defined between the first and second front waist-leg-peripheral-edges (18,18'), between the first and sixth positions (20,20',25,25'), wherein a second area (A2) is defined between the first and second back waist-leg-peripheral-edges (19,19'), between the third and fourth positions (23,23',24,24'), characterized in that distance D, extending parallel to the longitudinal axis (Y-Y) between the front waist end (13) and the fifth position (22,22'), is smaller than length L of a front waist lateral edge (15,15') extending parallel to the longitudinal axis (Y-Y), in that at least 50% of the total surface area of the chassis (2) comprises said elastic web material (12,12'), and each of the first and second areas (A1, A2) are substantially elastified, and in that the surface area of the elastified first area (A1) is from 3% to 35% of the surface area of the elastified second area (A2), as measured in an extended state, wherein a portion of the first and second front waist-leg-peripheral-edges (18,18') proximal to the front waist lateral edges (15,15') is substantially parallel to the front waist end (13), and wherein the liquid-absorbing core (9) extends over the elastic web material (12,12') along the longitudinal axis (Y-Y) and wherein both front and back ends (10,11) of the core (9) are disposed in the first and second areas (A1, A2) respectively such that at least 35% of the total surface area of said liquid-absorbing core (9) is comprised within the elastified first and second areas (A1, A2).

2. An absorbent article (1) according to claim 1, wherein each of the first and second front waist-leg-peripheral-edges (18,18') extend in an inward curved manner along opposite directions from the longitudinal axis (Y-Y).

3. An absorbent article (1) according to claim 1, wherein the ratio of distance D to length L is within the range 45% to 80%.

4. An absorbent article (1) according to claim 1, wherein a distance C between the sixth position (25,25') and the second position (21,21') and a distance E, where E=L-D, are interrelated so that E/C is within the range 10% to 35%.

5. An absorbent article (1) according to claim 4, wherein E/C is within the range 15% to 32%.

6. An absorbent article (1) according to claim 1, wherein a distance extending parallel to the longitudinal axis Y-Y between the first position (20,20') and the front waist end (13) is greater than L.

7. An absorbent article (1) according to claim 1, wherein the article is free from an elastic thread proximal and substantially parallel to the first and second front waist-leg-peripheral-edges (18,18').

8. An absorbent article (1) according to claim 1, wherein the surface area of the elastified first area (A1) is from 5% to 18% of the surface area of the elastified second area (A2), as measured in an extended state.

9. An absorbent article (1) according to claim 1, wherein at least 70% of the total surface area of the chassis (2) comprises the elastic web material (12,12').

10. An absorbent article (1) according to claim 1, wherein the first and second areas (A1, A2) comprise the elastic web material (12,12'), said material (12,12') being arranged to provide elasticity to said first and second areas (A1, A2).

11. An absorbent article (1) according to claim 1, wherein each of the first and second back waist-leg-peripheral-edges (19,19') extend substantially obliquely and along opposite directions from the longitudinal axis (Y-Y) such that the third position (23,23') and the fourth position (24,24') are separated along a first distance (A) extending parallel to the longitudinal axis (Y-Y), and further separated along a second distance (B) extending perpendicular to the longitudinal axis (Y-Y) and parallel to the transverse axis (X-X), and wherein the distance ratio (A/B) is greater than 0.5.

12. An absorbent article (1) according to claim 11, wherein the distance ratio (A/B) is between 0.5 and 0.8.

13. An absorbent article (1) according to claim 1, wherein the elastic web material (12,12') is selected from the group consisting of an elastic film, elastic fibers, elastic strings, elastic networks, elastic nonwovens, and combinations thereof.

14. An absorbent article (1) according to claim 1, wherein the portion of the crotch region between the first and second areas (A1,A2) comprises one or more nonelastic materials arranged such that said region is substantially inelastic.

15. An absorbent article (1) according to claim 1, wherein the absorbent article is an incontinence pant-like diaper.

16. An absorbent article (1) according claim 1, wherein the ratio of distance D to length L is within the range 50% to 75%.

17. An absorbent article (1) according to claim 1, wherein between 83% and 99% of the total surface area of the chassis (2) comprises the elastic web material (12,12').

18. An absorbent article (1) according to claim 1, wherein between 40% and 100% of the total surface area of said liquid-absorbing core (9) is comprised within the elastified first and second areas (A1, A2).

* * * * *